US012178630B2

(12) United States Patent
Sakuragi (10) Patent No.: US 12,178,630 B2
(45) Date of Patent: Dec. 31, 2024

(54) IMAGE ORIENTATION SETTING APPARATUS, IMAGE ORIENTATION SETTING METHOD, AND IMAGE ORIENTATION SETTING PROGRAM (71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 138 days.

(21) Appl. No.: 17/477,550

(22) Filed: Sep. 17, 2021

(65) Prior Publication Data
US 2022/0000442 A1 Jan. 6, 2022

Related U.S. Application Data (63) Continuation of application No. PCT/JP2020/012710, filed on Mar. 23, 2020.

(30) Foreign Application Priority Data

Apr. 25, 2019 (JP) .................... 2019-083994

(51) Int. Cl.
A61B 6/00 (2024.01)
A61B 6/46 (2024.01)
(Continued)

(52) U.S. Cl.
CPC .......... *A61B 6/5217* (2013.01); *A61B 6/466* (2013.01); *A61B 6/504* (2013.01); *G06T 19/00* (2013.01);
(Continued)

(58) Field of Classification Search
CPC ....... A61B 6/5217; A61B 6/466; A61B 6/504; G06T 19/00; G06T 2200/04; G06T 2210/41; G06T 2219/008
See application file for complete search history.

(56) References Cited

U.S. PATENT DOCUMENTS 7,369,691 B2    5/2008 Kondo et al.
7,929,799 B2 *  4/2011 Declerck ............... G06T 7/11
                                              382/173
(Continued)

FOREIGN PATENT DOCUMENTS

JP    2004283373    10/2004
JP    2009189557    8/2009
(Continued)

OTHER PUBLICATIONS

"International Search Report (Form PCT/ISA/210) of PCT/JP2020/012710," mailed on Jun. 23, 2020, with English translation thereof, pp. 1-5.
(Continued)

*Primary Examiner* — Abderrahim Merouan
(74) *Attorney, Agent, or Firm* — JCIPRNET (57) ABSTRACT A core-line extraction unit extracts a core line of the blood vessel from a three-dimensional image of a subject including the blood vessel. A local-route extraction unit extracts a local route of the core line within a predetermined range based on a reference point on the core line. In a case where a plurality of points on the local route are projected, a plane setting unit sets a plane having an orientation in which a distribution of a plurality of the projected points has a reference value based on a maximum value of the distribution, as a display plane of the three-dimensional image.

17 Claims, 9 Drawing Sheets (51) Int. Cl.
*A61B 6/50* (2024.01)
*G06T 19/00* (2011.01)
(52) U.S. Cl.
CPC ...... *G06T 2200/04* (2013.01); *G06T 2210/41* (2013.01); *G06T 2219/008* (2013.01)

(56) References Cited

U.S. PATENT DOCUMENTS

| | | | | |
|---|---|---|---|---|
| 9,600,895 | B2* | 3/2017 | Koceski | G06T 7/136 |
| 11,197,651 | B2* | 12/2021 | Cohen | A61B 5/7289 |
| 2004/0249270 | A1* | 12/2004 | Kondo | G06T 7/12 |
| | | | | 382/128 |
| 2006/0193510 | A1* | 8/2006 | Matsumoto | G06T 15/06 |
| | | | | 382/154 |
| 2009/0016483 | A1* | 1/2009 | Kawasaki | A61B 6/504 |
| | | | | 378/4 |
| 2009/0087068 | A1* | 4/2009 | Sakaguchi | A61B 6/504 |
| | | | | 382/154 |
| 2009/0207965 | A1 | 8/2009 | Sakaguchi | |
| 2011/0227912 | A1 | 9/2011 | Sugama | |
| 2012/0026162 | A1* | 2/2012 | Masumoto | G06T 19/00 |
| | | | | 345/419 |
| 2012/0249615 | A1* | 10/2012 | Lee | G09G 3/3233 |
| | | | | 345/691 |
| 2013/0064343 | A1* | 3/2013 | Verstraelen | A61B 6/469 |
| | | | | 378/4 |
| 2014/0088416 | A1* | 3/2014 | Sakuragi | G06T 7/12 |
| | | | | 600/425 |
| 2014/0328529 | A1* | 11/2014 | Koceski | G06T 7/174 |
| | | | | 382/131 |
| 2018/0310899 | A1* | 11/2018 | Garlow | A61B 6/5205 |
| 2019/0197762 | A1* | 6/2019 | Inoue | G06T 19/00 |
| 2019/0201691 | A1* | 7/2019 | Poltorak | A61B 5/165 |
| 2019/0236776 | A1* | 8/2019 | Miyamoto | G06T 7/11 |
| 2019/0266723 | A1* | 8/2019 | Blanchard | G06V 20/698 |
| 2021/0145608 | A1* | 5/2021 | Herr | A61B 8/0825 |
| 2022/0000442 | A1* | 1/2022 | Sakuragi | G06T 19/00 |

FOREIGN PATENT DOCUMENTS

| | | |
|---|---|---|
| JP | 2011197816 | 10/2011 |
| JP | 2016073501 | 5/2016 |
| JP | 2016087139 | 5/2016 |
| JP | 2016143321 | 8/2016 |
| JP | 2016202247 | 12/2016 |

OTHER PUBLICATIONS

"Written Opinion of the International Searching Authority (Form PCT/ISA/237)" of PCT/JP2020/012710, mailed on Jun. 23, 2020, with English translation thereof, pp. 1-10.

"Office Action of Japan Counterpart Application", issued on May 10, 2022, with English translation thereof, p. 1-p. 10.

* cited by examiner

IMAGE ORIENTATION SETTING APPARATUS, IMAGE ORIENTATION SETTING METHOD, AND IMAGE ORIENTATION SETTING PROGRAM

CROSS-REFERENCE TO RELATED APPLICATIONS

This application is a Continuation of PCT International Application No. PCT/JP2020/012710 filed on Mar. 23, 2020, which claims priority under 35 U.S.C § 119(a) to Japanese Patent Application No. 2019-083994 filed on Apr. 25, 2019. Each of the above application(s) is hereby expressly incorporated by reference, in its entirety, into the present application.

BACKGROUND OF THE INVENTION

1. Field of the Invention

The present disclosure relates to an image orientation setting apparatus, an image orientation setting method, and an image orientation setting program, which set an orientation of an image in a case where a three-dimensional image including a blood vessel is displayed.

2. Description of the Related Art

Hitherto, a contrast-enhanced radiographic image diagnosis apparatus has been used, in order to perform examination of the shape of a blood vessel, an abnormality of the blood vessel, a state of blood flow, and the like and treatment. The contrast-enhanced radiographic image diagnosis apparatus is called an angiography apparatus. In the angiography apparatus, a contrast agent is injected into a blood vessel by using a catheter, and a patient with the contrast agent injected is imaged, so that an angiographic image which is a radiographic image of the blood vessel is acquired. Since the examination and treatment using the angiography apparatus can be performed while the blood flow distribution and the state of the blood vessel, such as hemadostenosis, are confirmed with the angiographic image, the examination and treatment can be efficiently performed.

Meanwhile, advances in medical equipment such as a computed tomography (CT) apparatus and a magnetic resonance imaging (MRI) apparatus have made it possible to use a high quality three-dimensional image having high resolution for diagnostic imaging. Therefore, in a case where the examination and treatment using the above-described angiography apparatus are performed, a three-dimensional image including the blood vessel contrast-enhanced with a contrast agent has been acquired by using a CT apparatus, and the simulation of the examination and treatment has been performed by using the three-dimensional image. For example, processing of generating a projected image, such as a ray-sum image, which is a pseudo radiographic image projected through the addition and average of pixels of the three-dimensional image in one direction, and emphasizing the contour of the blood vessel in the projected image has made it possible to perform the simulation of the examination and treatment using the angiography apparatus. In the angiography apparatus, since the examination and treatment are performed while the subject is irradiated with radiation, the subject and the doctor are exposed to a large dose of radiation. The examination and treatment time can be shortened in a case where simulation is performed before the examination and treatment using the angiography apparatus, so that the exposure dose to the subject and the doctor can be reduced.

Incidentally, since blood vessels travel three-dimensionally in a complicated manner, it is difficult to find the position and state of a lesion, such as hemadostenosis and aneurysm, even in a case where the above-described projected image is observed. Therefore, a method has been proposed in which the core line of a blood vessel is extracted from a three-dimensional image, and at least one image of an extension image of the blood vessel based on the extracted core line or an orthogonal cross-sectional image orthogonal to the core line is created (JP2004-283373A). According to the method described in JP2004-283373A, since the generated image is displayed, a lesion, such as hemadostenosis and aneurysm, can be easily observed.

SUMMARY OF THE INVENTION

Meanwhile, in a case where simulation is performed before examination and treatment using an angiography apparatus, it is necessary to make sure of along which route in the blood vessel the catheter should be advanced to reach a target position, such as hemadostenosis and aneurysm. However, the blood vessel branches or changes the orientation thereof to three-dimensionally travel in a complicated manner. Therefore, it is difficult to know along which route in the blood vessel the catheter should be advanced to reach the target position even in a case where the extension image and the orthogonal cross-sectional image described in JP2004-283373A described above are observed.

The present disclosure has been made in view of the above circumstances, and an object thereof is to enable a three-dimensional image to be displayed in an orientation in which a travel state of a blood vessel can be appropriately observed.

An image orientation setting apparatus according to the present disclosure comprises:
  a core-line extraction unit that extracts a core line of a blood vessel from a three-dimensional image of a subject including the blood vessel;
  a local-route extraction unit that extracts a local route of the core line within a predetermined range based on a reference point on the core line; and
  a plane setting unit that sets, in a case where a plurality of points on the local route are projected, a plane having an orientation in which a distribution of a plurality of the projected points has a reference value based on a maximum value of the distribution, as a display plane of the three-dimensional image.

In the image orientation setting apparatus according to the present disclosure, in a case where the reference point is moved, the local-route extraction unit may extract the local route within the predetermined range based on the moved reference point, and
  the plane setting unit may set the display plane on the basis of the local route extracted within the predetermined range based on the moved reference point.

In this case, the plane setting unit may generate at least one interpolation display plane that is interpolated between a first display plane set on the basis of the local route extracted within the predetermined range based on the reference point before the movement and a second display plane set on the basis of the local route extracted within the predetermined range based on the reference point after the movement.

Further, in the image orientation setting apparatus according to the present disclosure, the local-route extraction unit may change a range of the local route in response to a change instruction of the predetermined range.

Further, in the image orientation setting apparatus according to the present disclosure, the reference point may be located between a start point and a target point set on the core line.

Further, in the image orientation setting apparatus according to the present disclosure, the plane setting unit may set a plane having an orientation in which a sum of distances from the plurality of points is minimized, as the display plane.

Further, in the image orientation setting apparatus according to the present disclosure, the plane setting unit may set the display plane within a predetermined angle range from a reference angle.

In addition, in the image orientation setting apparatus according to the present disclosure, a display control unit that displays a projected image in which the three-dimensional image with the blood vessel emphasized is projected onto the display plane, on a display unit may further be provided.

Further, in the image orientation setting apparatus according to the present disclosure, the display control unit may emphasize the blood vessel with the core line superimposed thereon, and display the projected image.

Further, in the image orientation setting apparatus according to the present disclosure, the display control unit may emphasize the local route in the core line, and display the projected image.

An image orientation setting method according to the present disclosure comprises:
   extracting a core line of a blood vessel from a three-dimensional image of a subject including the blood vessel;
   extracting a local route of the core line within a predetermined range based on a reference point on the core line; and
   setting, in a case where a plurality of points on the local route are projected, a plane having an orientation in which a distribution of a plurality of the projected points has a reference value based on a maximum value of the distribution, as a display plane of the three-dimensional image.

The image orientation setting method according to the present disclosure may also be provided as a non-transitory computer readable recording medium storing a program to be executed by a computer.

Another image orientation setting apparatus according to the present disclosure comprises:
   a memory that stores a command to be executed by a computer; and
   a processor configured to execute the stored command, in which the processor executes processing of
      extracting a core line of a blood vessel from a three-dimensional image of a subject including the blood vessel,
      extracting a local route of the core line within a predetermined range based on a reference point on the core line, and
      setting, in a case where a plurality of points on the local route are projected, a plane having an orientation in which a distribution of a plurality of the projected points has a reference value based on a maximum value of the distribution, as a display plane of the three-dimensional image.

According to the present disclosure, a three-dimensional image can be displayed so as to have an orientation in which the travel state of a blood vessel can be appropriately observed.

DESCRIPTION OF THE PREFERRED EMBODIMENTS

Figure 1:
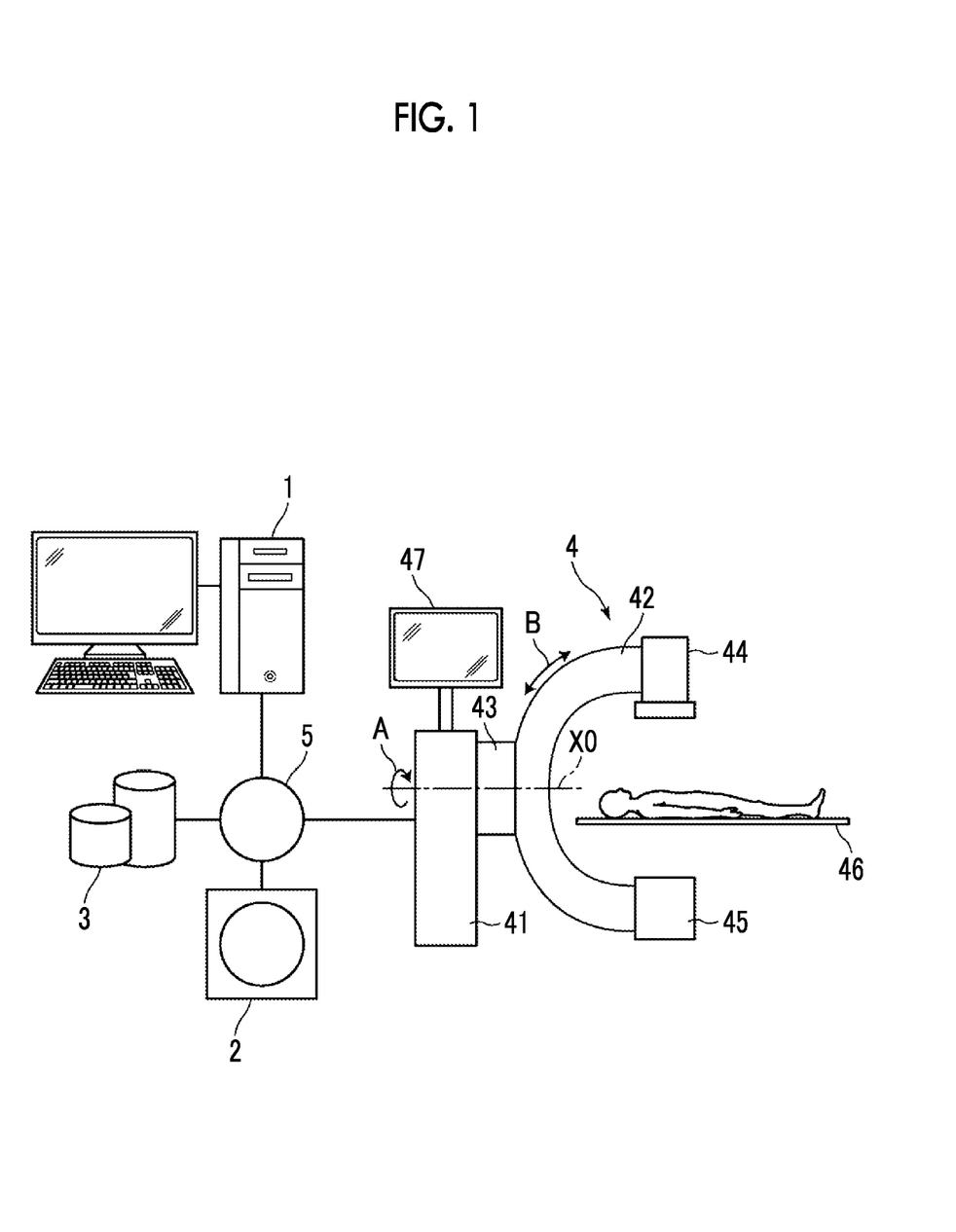
FIG. 1 is a diagram showing an outline of a diagnosis support system to which an image orientation setting apparatus according to an embodiment of the present disclosure is applied.

Hereinafter, an embodiment of the present disclosure will be described with reference to the drawings. FIG. 1 is a hardware configuration diagram showing an outline of a diagnosis support system to which an image orientation setting apparatus according to the embodiment of the present disclosure is applied. As shown in FIG. 1, in the system, an image orientation setting apparatus 1, a three-dimensional image capturing apparatus 2, an image storage server 3, an angiography apparatus 4 according to the present embodiment are connected to communicate with one another via a network 5.

The three-dimensional image capturing apparatus 2 is an apparatus that images an area to be diagnosed of a subject and generates a three-dimensional image representing the area, and specific examples thereof include a CT apparatus, an MRI apparatus, and a positron emission tomography (PET) apparatus. The three-dimensional image generated by the three-dimensional image capturing apparatus 2 is transmitted to and stored in the image storage server 3. In the present embodiment, the area to be diagnosed of the subject is a blood vessel, such as an aorta and an artery branching from the aorta, the three-dimensional image capturing apparatus 2 is a CT apparatus, and a three-dimensional image is a CT image including the blood vessel of the subject into which a contrast agent is injected.

The image storage server 3 is a computer that stores and manages various data, and comprises a large-capacity external storage device and database management software. The image storage server 3 communicates with another apparatus via a wired or wireless network 5 to transmit and receive image data and the like. Specifically, the image storage server 3 acquires the image data, such as the three-dimensional image generated by the three-dimensional image capturing apparatus 2, via the network, and stores and manages the acquired image data in a recording medium, such as a large-capacity external storage device. A storage format of the image data and the communication between the apparatuses via the network 5 are based on a protocol such as digital imaging and communication in medicine (DICOM). Further, a tag based on the DICOM standard is given to the three-dimensional image. The tag includes information, such as a patient name, information representing an imaging apparatus, an imaging date and time, and an imaging area.

An angiography apparatus 4 is an apparatus that is used to perform examination of the shape of the blood vessel of the subject, the abnormality of the blood vessel, the state of blood flow, and the like, and treatment. In the angiography apparatus 4, a C arm 42 is attached to a main body 41 through an attachment portion 43 so as to be rotatable around an axis X0, that is, in an arrow A direction. Further, the C arm 42 is attached to the attachment portion 43 so as to be movable in an arrow B direction shown in FIG. 1. A radiation source 44 is attached to one end of the C arm 42, and an imaging unit 45 is attached to the other end. The imaging unit 45 has a built-in radiation detector that is used to detect the radiation transmitted through the subject on an imaging table 46 and generate a radiographic image. Further, a display unit 47, such as a liquid crystal display, which is used to display an angiographic image of the subject imaged by the angiography apparatus 4 or display various information relating to examination and treatment using the angiography apparatus 4 is attached to the main body 41. The doctor examines and treats the blood vessel while looking at the angiographic image displayed on the display unit 47. In the present embodiment, the examination and treatment of the aorta and the artery branching from the aorta are performed by the angiography apparatus 4.

The image orientation setting apparatus 1 is configured with the image orientation setting program of the present embodiment installed on one computer. The computer may be a workstation or a personal computer directly operated by the doctor who makes diagnosis, or may be a server computer connected to the workstation or the personal computer via the network. The image orientation setting program is stored in a storage device of a server computer connected to the network or a network storage so as to be accessible from the outside, and is downloaded and installed on the computer that the doctor uses according to a request. Alternatively, the image orientation setting program is recorded in a recording medium, such as a digital versatile disc (DVD) or a compact disc read only memory (CD-ROM), and distributed, and is installed on a computer from the recording medium.

Figure 2:
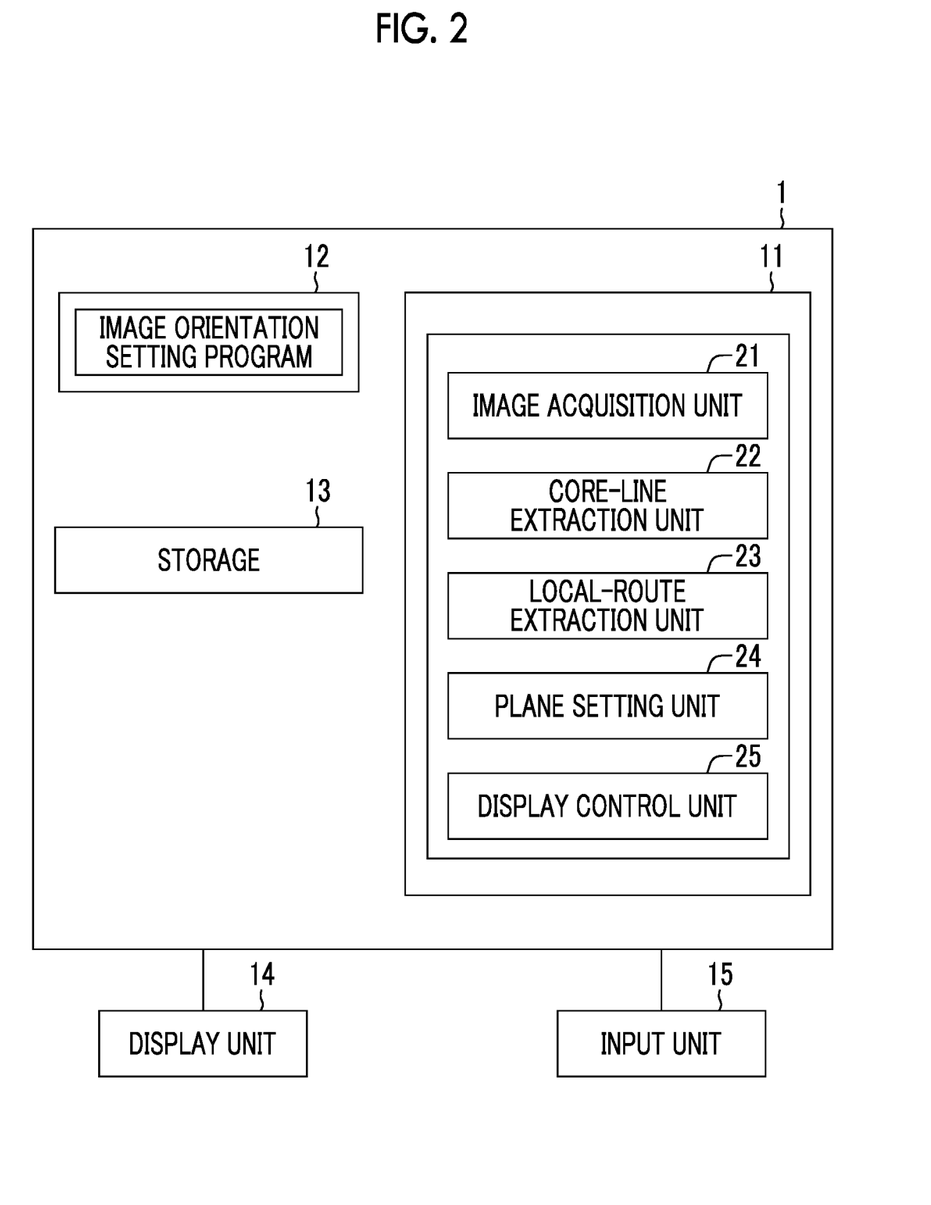
FIG. 2 is a diagram showing a schematic configuration of the image orientation setting apparatus which is realized with an image orientation setting program installed on a computer.

FIG. 2 is a diagram showing the schematic configuration of the image orientation setting apparatus which is realized with the image orientation setting program installed on a computer. As shown in FIG. 2, the image orientation setting apparatus 1 comprises a CPU 11, a memory 12, and a storage 13, as a standard workstation configuration. Further, a display unit 14, such as a liquid crystal display, and an input unit 15, such as a mouse, are connected to the image orientation setting apparatus 1. A touch panel that serves as the display unit 14 and the input unit 15 may be used.

The storage 13 stores various information including a three-dimensional image acquired from the image storage server 3 via the network 5 and a projected image generated by processing by the image orientation setting apparatus 1.

Further, the image orientation setting program is stored in the memory 12. The image orientation setting program defines, as processing to be executed by the CPU 11, image acquiring processing of acquiring a three-dimensional image of a subject including a blood vessel contrast-enhanced with a contrast agent, core-line extracting processing of extracting a core line of the blood vessel from the three-dimensional image, local-route extracting processing of extracting a local route of the core line within a predetermined range based on a reference point on the core line, plane setting processing of setting, in a case where a plurality of points on the local route are projected, a plane having an orientation in which a distribution of a plurality of the projected points has a reference value based on a maximum value of the distribution, as a display plane of the three-dimensional image, and display controlling processing of displaying a projected image in which the three-dimensional image is projected onto the display plane, on the display unit 14.

The CPU 11 executes the processing according to the program, so that the computer functions as an image acquisition unit 21, a core-line extraction unit 22, a local-route extraction unit 23, a plane setting unit 24, and a display control unit 25.

The image acquisition unit 21 acquires a three-dimensional image V0 to be processed including a contrast-enhanced blood vessel from the image storage server 3 via an interface (not shown) connected to the network. In a case where the three-dimensional image V0 is already stored in the storage 13, the image acquisition unit 21 may acquire the three-dimensional image V0 from the storage 13.

The core-line extraction unit 22 extracts the core line in a blood vessel region (hereinafter, referred to as a contrast-enhanced blood vessel region) contrast-enhanced from the three-dimensional image V0. The core line is a line representing a travel route of a blood vessel, for example, a line passing through a central position of a cross-section perpendicular to blood flow in the blood vessel. The core-line extraction unit 22 extracts the core line of the contrast-enhanced blood vessel region from the three-dimensional image V0 by using the methods described in, for example, JP2010-200925A and JP2010-220742A. In the methods, the positions of a plurality of candidate points constituting the core line of the blood vessel and the principal axis direction are first calculated on the basis of the values of voxel data constituting the three-dimensional image V0. Alternatively, the Hessian matrix is calculated for the three-dimensional image V0, and the calculated eigenvalues of the Hessian matrix are analyzed, so that the position information of the plurality of candidate points constituting the core line of the blood vessel and the principal axis direction are calculated. Then, a feature amount representing blood vessel-likeness is calculated for the voxel data around the candidate point, and determination is made whether or not the voxel data represents the blood vessel on the basis of the calculated feature amount. The determination based on the feature amount is made on the basis of the evaluation function acquired in advance by machine learning. As a result, the contrast-enhanced blood vessel region and the core line are extracted from the three-dimensional image V0. The core line may be extracted through the extraction of the contrast-enhanced blood vessel region and then thinning processing on the extracted contrast-enhanced blood vessel region.

Figure 3:
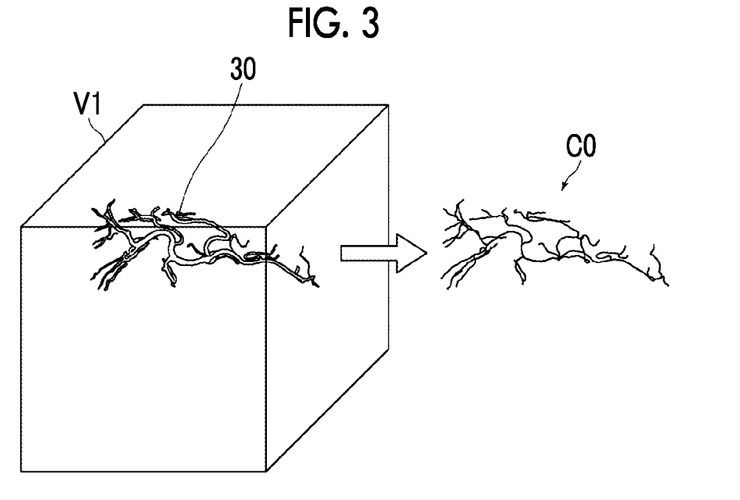
FIG. 3 is a diagram for explaining extraction of a core line from a three-dimensional image.

FIG. 3 is a diagram for explaining the extraction of the core line from the three-dimensional image V0. Here, the extraction of the core line from a partial three-dimensional image V1 representing a part of region of the three-dimensional image will be described. As shown in FIG. 3, the partial three-dimensional image V1 includes a contrast-enhanced blood vessel region 30. The core-line extraction unit 22 extracts the core line C0 of the contrast-enhanced blood vessel region 30 included in the partial three-dimensional image V1.

Figure 4:
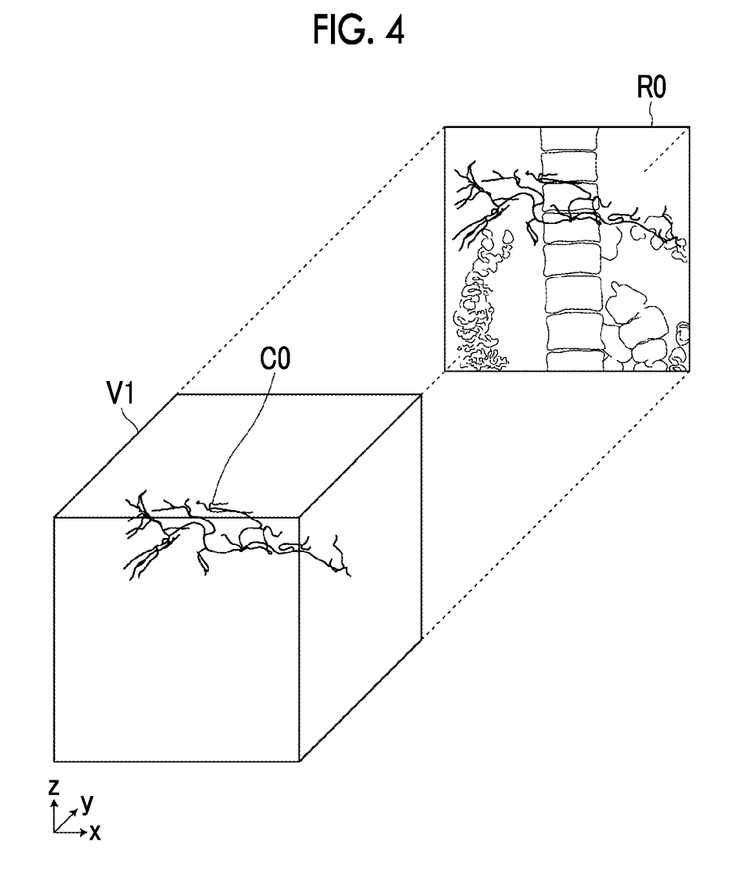
FIG. 4 is a diagram for explaining generation of a ray-sum image.

In a case where the core line C0 is extracted, the display control unit 25 performs perspective projection on the three-dimensional image V0 and ray-sum rendering processing, to generate a ray-sum image which is a pseudo radiographic image of the subject. In this case, the display control unit 25 emphasizes the blood vessel region with the core line C0 superimposed on the blood vessel region in the ray-sum image. FIG. 4 is a diagram for explaining the generation of the ray-sum image. Here, the generation of a ray-sum image for a partial three-dimensional image representing a part of region of the three-dimensional image will be described. As shown in FIG. 4, the display control unit 25 performs perspective projection on the partial three-dimensional image V1 representing a part of region of the three-dimensional image V0 in a y direction shown in FIG. 4 and ray-sum rendering in which the addition and average of pixel values of pixels arranged in the y direction are calculated, to generate a ray-sum image R0. In the present embodiment, in FIG. 4 and the following description, it is assumed that an x direction coincides with the right and left direction of the subject, the y direction coincides with the back and forth direction of the subject, and a z direction coincides with the body axis direction of the subject. Therefore, the ray-sum image R0 is a pseudo image representing a radiographic image generated by imaging the subject from the front. The plane on which the three-dimensional image V0 is projected in order to generate the ray-sum image R0 generated in this way, that is, the display plane is a reference display plane, and the orientation of the reference display plane is a reference orientation that is used to initially display the three-dimensional image V0. Here, in the present embodiment, upon the ray-sum rendering, the CT value is converted such that the larger the CT value, the higher the density (that is, blacker), but the CT value may be converted such that the larger the CT value, the lower the density (that is, whiter).

The emphasis of the blood vessel region is not limited to superimposing the core line C0. The blood vessel region may be emphasized through the projection of the blood vessel region by maximum value projection, the coloring of the blood vessel region, or the like.

In the present embodiment, the display control unit 25 first displays the ray-sum image R0 in the above-described reference orientation, on the display unit 14. The operator sets a start point and a target point of the blood vessel region to be observed, on the core line C0 superimposed on the ray-sum image R0 displayed on the display unit 14. Further, a reference point for which detailed display is desired is set between the start point and the target point. Here, in a case where the blood vessel is an aorta or an artery branching from the aorta, the target point is a position in which the catheter is reached and the examination and treatment performed, in the artery to be diagnosed. The start point is, for example, the branch position of the artery that the catheter first reaches in a case where the catheter is inserted into the aorta from the leg joint. The reference point is, for example, the branch position of the artery that the catheter first reaches between the start point and the target point.

Figure 5:
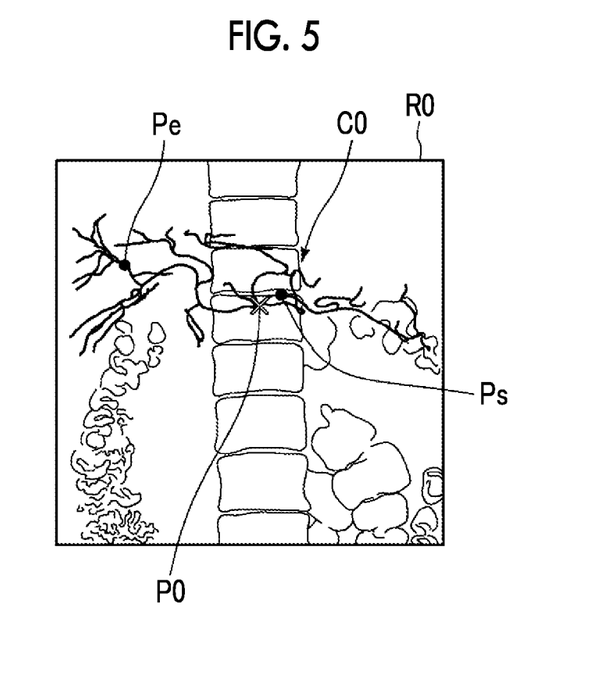
FIG. 5 is a diagram for explaining setting of a start point, a target point, and a reference point in the core line C0.

FIG. 5 is a diagram for explaining the setting of the start point, the target point, and the reference point on the core line C0. As shown in FIG. 5, in the displayed ray-sum image R0, the operator sets the observation start point Ps and the target point Pe by using the input unit 15. Further, the operator sets a reference point P0 between the start point Ps and the target point Pe. The reference point P0 set in the ray-sum image R0 having the reference orientation is an initial reference point.

Figure 6:
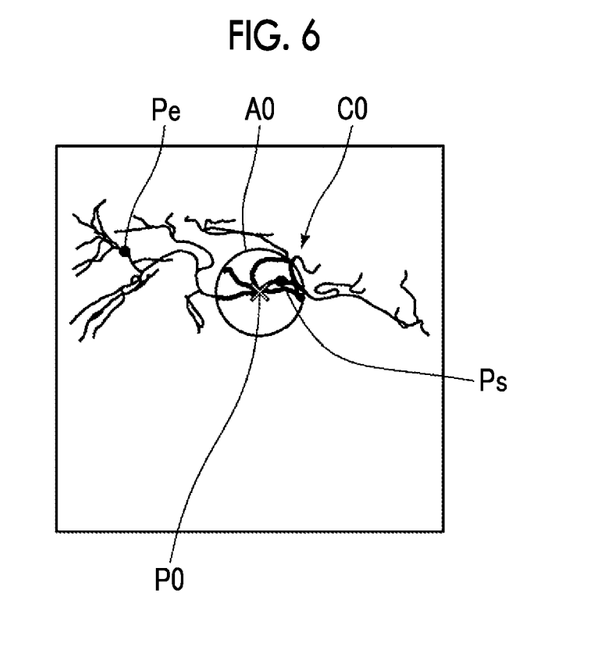
FIG. 6 is a diagram for explaining extraction of a local route.

The local-route extraction unit 23 extracts a local route of the core line C0 within a predetermined range based on the reference point P0 on the core line C0. FIG. 6 is a diagram for explaining the extraction of the local route. The local-route extraction unit 23 sets a sphere A0 having a predetermined size centered on the reference point P0 in the three-dimensional image V0. Then, in the sphere A0, the core line C0 passing through the reference point P0 is extracted as a local route L0. In FIG. 6, the sphere A0 (a circle in FIG. 6) is set in the ray-sum image R0, and the core line C0 passing through the reference point P0 in the sphere A0 is indicated by a thick line, so that the local route L0 is emphasized. The emphasis of the local route L0 is not limited thereto. The local route L0 may be emphasized through the coloring of the local route L0 or the like.

Figure 7:
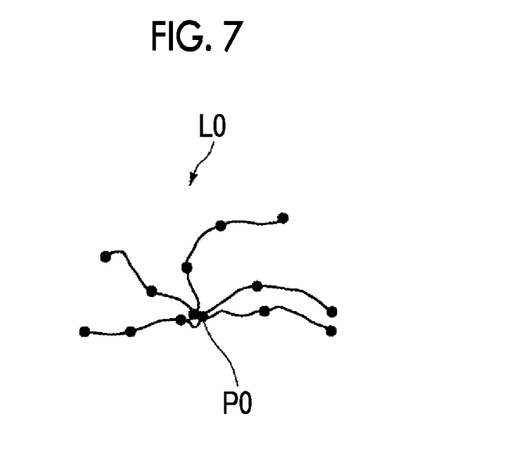
FIG. 7 is a diagram showing a plurality of points set in the local route.

In a case where a plurality of points on the local route L0 are projected, the plane setting unit 24 sets a plane having an orientation in which a distribution of a plurality of the projected points has a reference value, as a display plane of the three-dimensional image V0. In the present embodiment, the reference value is the maximum value of the distribution of the plurality of projected points. First, as shown in FIG. 7, the plane setting unit 24 sets the plurality of points on the local route L0. The intervals between the points may be equal intervals or any intervals. Further, the number of points may be appropriately set according to the size of the local route L0 and the amount of arithmetic operation. Here, the plane having the orientation in which the distribution of the plurality of projected points on the local route L0 has the maximum value is a plane having an orientation in which the sum of distances from each point is minimized. The distance from each point to the plane is the distance between each point and the intersection of each point on the line, which passes through each point and is orthogonal to the plane, and the plane.

Figure 8:
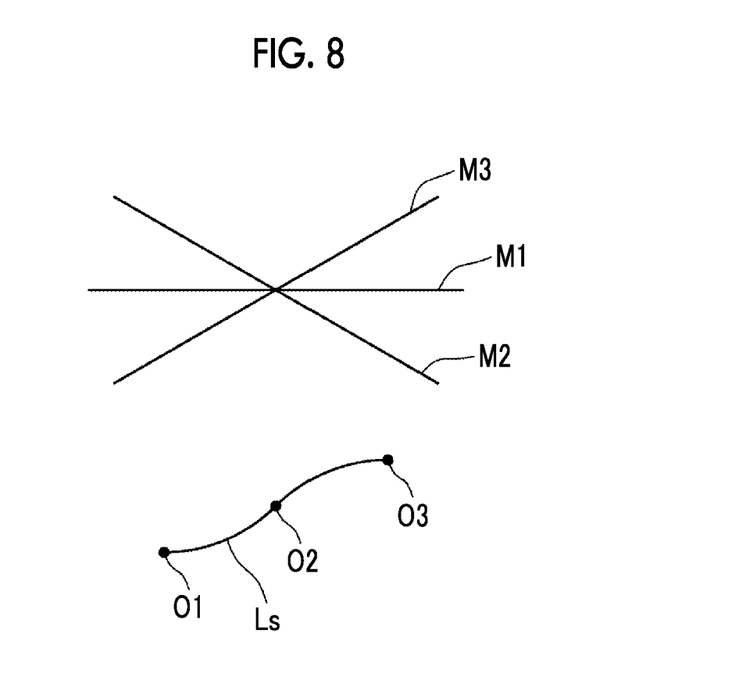
FIG. 8 is a diagram for explaining setting of a display plane.

Therefore, the plane setting unit 24 sets the plane having the orientation in which the sum of the distances from each point on the local route L0 is minimized, as the display plane of the three-dimensional image V0. FIG. 8 is a diagram for explaining the setting of the display plane. In FIG. 8, for simplification of explanation, three points O1 to O3 are set on one local route Ls, and three planes (lines in FIG. 8) M1 to M3 having different orientations are shown. In a case where the sum of the distances from the three points O1 to O3 for each of the three planes M1 to M3 is calculated, the sum of the distances from the three points O1 to O3 to the plane M3 is minimized.

The plane setting unit 24 first sets a tentative plane, and calculates the sum of the distances between the tentative plane and the points set on the local route L0. Then, the change of the orientation of the tentative plane, the setting of a tentative plane after the change, the calculation of the sum of the distances are repeated, so that a tentative plane in which the sum of the distances is minimized is set as the display plane of the three-dimensional image V0. In the situation shown in FIG. 8, the plane setting unit 24 sets the plane M3 as the display plane of the three-dimensional image V0.

In the present embodiment, a ray-sum image is generated from the three-dimensional image V0 of the subject for the simulation of the examination and the treatment performed by the angiography apparatus 4. Here, in the angiography apparatus 4, the C arm 42 is rotated around the axis X0 in the arrow A direction in FIG. 1 and moves in the arrow B direction. However, the rotation and movement of the C arm 42 are restricted due to the structure of the angiography apparatus 4. For example, as shown in FIG. 1, the rotation angle of the C arm 42 around the axis X0 is about ±60 degrees from the reference position where the C arm 42 is located at a position in which the subject can be imaged from the front. Further, the movement of the C arm 42 in the arrow B direction is 30 degrees (that is, ±30 degrees) in the clockwise direction and the counterclockwise direction from the reference position, respectively.

Figure 9:
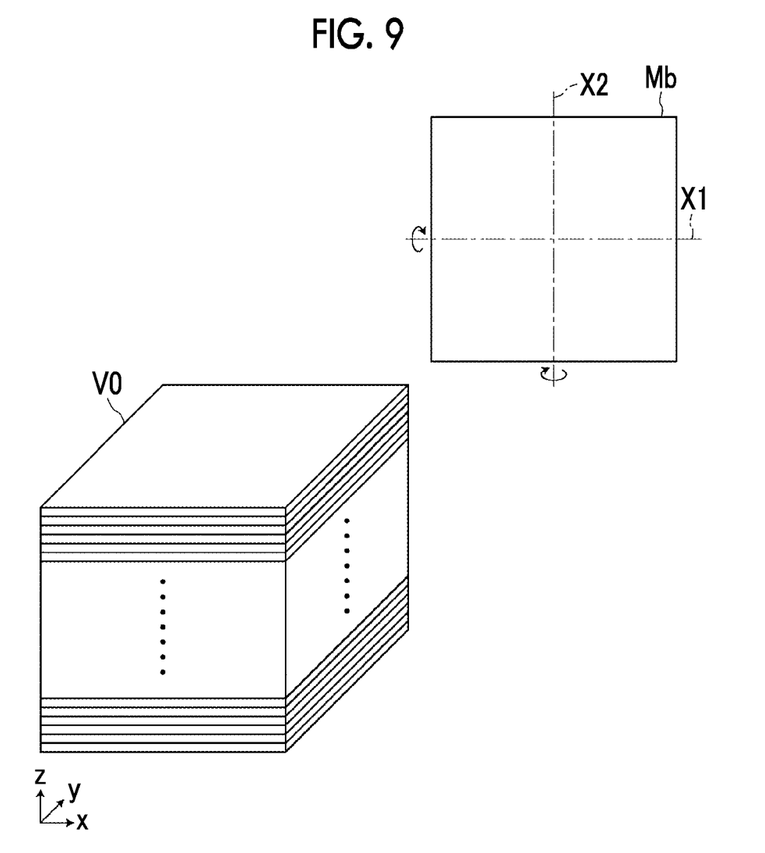
FIG. 9 is a diagram for explaining restriction of inclination of the display plane.

Therefore, it is preferable that the orientation of the display plane set by the plane setting unit 24 is also restricted to correspond to the angiography apparatus 4. For example, as shown in FIG. 9, an axis X1 extending in the x direction and an axis X2 extending in the z direction are set on a reference display plane Mb on which the three-dimensional image V0 is projected in order to generate the ray-sum image R0 shown in FIG. 4. The axis X1 is the center of rotation of the display plane caused by the movement of the C arm 42 in the arrow B direction, and the axis X2 is the center of rotation of the display plane caused by the rotation of the C arm 42 in the arrow A direction. Therefore, the plane setting unit 24 restricts the orientation of the display plane to ±30 degrees around the axis X1 and ±60 degrees around the axis X2, on the basis of the reference display plane Mb. With regard to the angles around the axes X1 and X2, the reference angle is 0 degrees. Meanwhile, in a case where the orientation of the display plane to be set deviates from the restricted angle, the plane setting unit 24 sets the display plane such that the orientation is inclined to the maximum at the restricted angle.

In a case where the orientation of the display plane deviates from the restricted angle, the display control unit 25 may issue a warning. The warning may be displayed, for example, on the display unit 14 with text indicating that the orientation of the display plane deviates from the restricted angle. Alternatively, the warning may be a sound, such as voice, or may be both a sound and a text.

Figure 10:
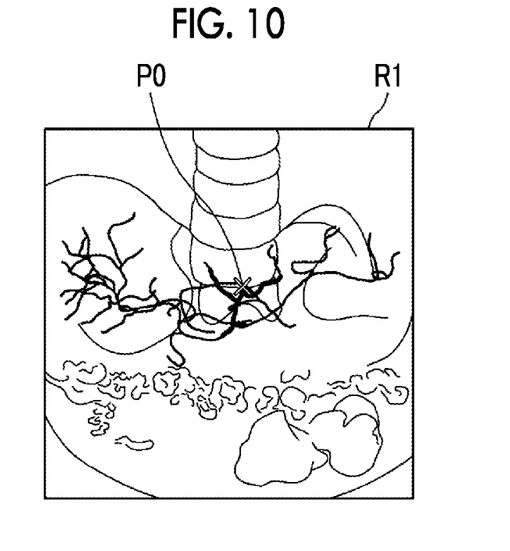
FIG. 10 is a diagram showing the ray-sum image that is generated by projecting the three-dimensional image onto the set display plane.

The display control unit 25 projects the three-dimensional image V0 onto a newly set display plane, and further generates a ray-sum image R1 with the core line C0 superimposed thereon. Further, the display control unit 25 emphasizes the local route in the ray-sum image R1. FIG. 10 is a diagram showing the ray-sum image generated by projecting the three-dimensional image V0 onto the set display plane. As shown in FIG. 10, in the ray-sum image R1, a viewing direction of the three-dimensional image V0 is different from that of the ray-sum image R0 in which the three-dimensional image V0 is projected onto the reference display plane Mb. Therefore, the shape of the core line C0 superimposed on the ray-sum image R1 is different from that of the ray-sum image R0.

Figure 11:
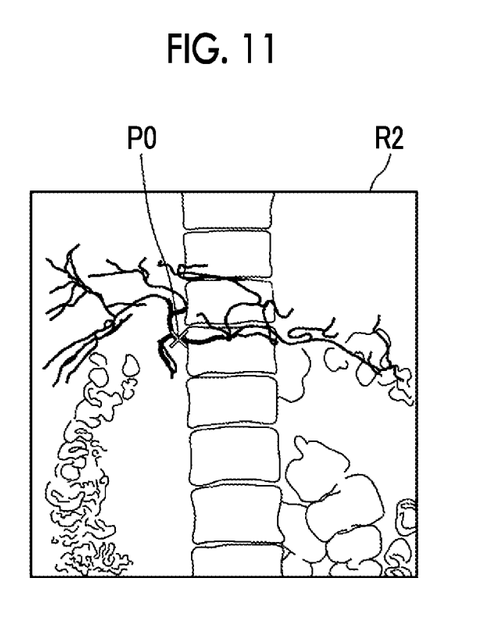
FIG. 11 is a diagram showing a newly displayed ray-sum image.
Figure 12:
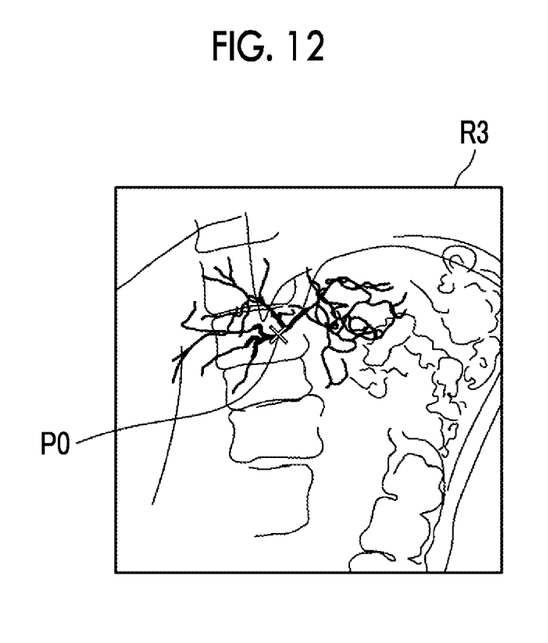
FIG. 12 is a diagram showing a newly displayed ray-sum image.

Furthermore, in a case where the operator moves the reference point by using the input unit 15 in the displayed ray-sum image, the local-route extraction unit 23 extracts a new local route on the basis of the new reference point after the movement, the plane setting unit 24 sets a new display plane, and the display control unit 25 projects the three-dimensional image V0 onto the new display plane and displays the ray-sum image on the display unit 14. FIGS. 11 and 12 are diagrams showing the newly displayed ray-sum images. The ray-sum image R2 shown in FIG. 11 is an image displayed after the ray-sum image R1 in which the reference point in the ray-sum image R1 is moved. The ray-sum image R3 shown in FIG. 12 is an image displayed after the ray-sum image R2 in which the reference point in the ray-sum image R2 is moved.

Figure 13:
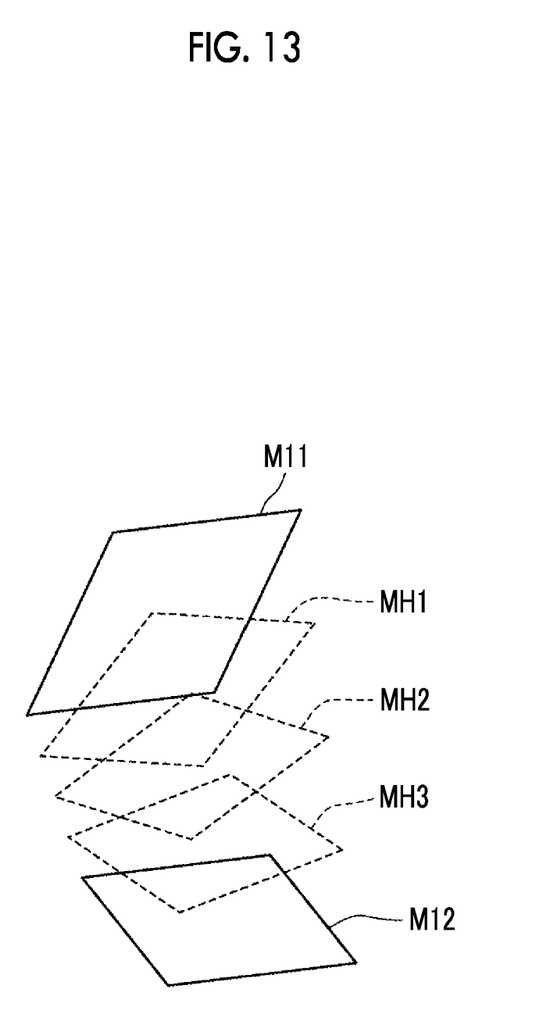
FIG. 13 is a diagram for explaining generation of interpolation display planes.

Here, in the ray-sum images R0 to R3, the orientations in which the three-dimensional image V0 is projected are different from one another. Therefore, in a case where the reference point is moved and the ray-sum image is switched, the orientation in which the three-dimensional image V0 is projected is changed abruptly, which makes it difficult to see the image. Therefore, in the present embodiment, the plane setting unit 24 generates at least one interpolation display plane that is interpolated between a first display plane generated on the basis of the reference point before the movement and a second display plane generated on the basis of the moved reference point. FIG. 13 is a diagram for explaining the generation of the interpolation display plane. As shown in FIG. 13, between a first display plane M11 generated on the basis of the reference point before the movement and a second display plane M12 generated on the basis of the moved reference point, three interpolation display planes MH1 to MH3 are generated so that the orientations of the display planes from the first display plane M1 to the second display plane M12 are gradually changed. The number of interpolation display planes is not limited to three, and may be two or less or four or more.

The display control unit 25 may generate the interpolation display plane only in a case where the inclination of the display plane due to the movement of the reference point becomes a predetermined threshold value or more.

The display control unit 25 projects the three-dimensional image V0 onto the interpolation display planes MH1 to MH3 to generate interpolation ray-sum images, and sequentially displays the interpolation ray-sum images between a ray-sum image R11 in which the three-dimensional image V0 is projected onto the display plane M11 and a ray-sum image R12 in which the three-dimensional image V0 is projected onto the display plane M12 in a case where the ray-sum images R11 and R12 are switched. As a result, the change from the ray-sum images R11 to R12 are smoothly performed.

Figure 14:
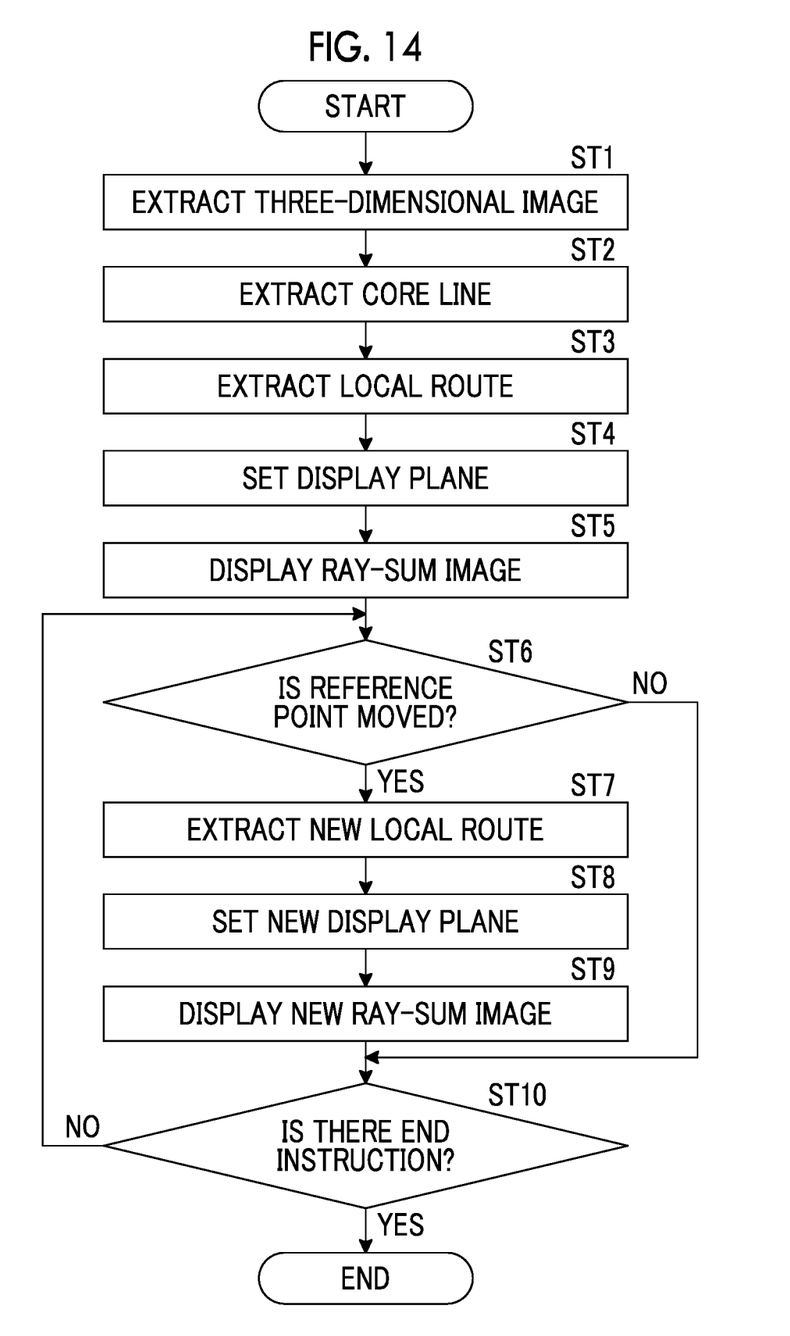
FIG. 14 is a flowchart showing processing performed in the present embodiment.

Next, processing performed in the present embodiment will be described. FIG. 14 is a flowchart showing processing performed in the present embodiment. First, the image acquisition unit 21 acquires the three-dimensional image V0 (Step ST1), and the core-line extraction unit 22 extracts the core line of the blood vessel from the three-dimensional image V0 (Step ST2). Next, the local-route extraction unit 23 extracts the local route of the core line within a predetermined range based on the reference point on the core line (Step ST3). Further, the plane setting unit 24 sets the display plane of the three-dimensional image V0 (Step ST4). Then, the display control unit 25 displays the ray-sum image in which the three-dimensional image V0 is projected onto the display plane, on the display unit 14 (Step ST5).

Next, determination is made whether or not the reference point is moved in response to the instruction of the operator (Step ST6). In a case where negative determination is made in Step ST6, the process proceeds to Step ST10. In a case where affirmative determination is made in Step ST6, the local-route extraction unit 23 extracts a new local route on the basis of the new reference point after the movement (Step ST7), the plane setting unit 24 sets a new display plane (Step ST8), and the display control unit 25 projects the three-dimensional image V0 onto the new display plane and displays anew ray-sum image (Step ST9). In the processing in Step ST8, the interpolation display planes are generated as necessary. In a case where the interpolation display planes are generated, the interpolation ray-sum images generated by projecting the three-dimensional image V0 onto the interpolation display planes are sequentially displayed between the displays of the ray-sum image displayed in Step ST5 and the new ray-sum image to be switched.

In a case where subsequent to Step ST9, determination is made whether or not the end instruction is given by the operator (Step ST10) and negative determination is made in Step ST10, the process returns to Step ST6, and the processing after Step ST6 are repeated. In a case where affirmative determination is made in Step ST10, the processing ends.

As described above, in the present embodiment, in a case where the local route of the core line is extracted and the plurality of points included in the local route are projected, the plane having the orientation in which the distribution of the plurality of projected points has the reference value based on the maximum value of the distribution is set as the display plane of the three-dimensional image V0. For this reason, the three-dimensional image V0 displayed on the display plane has an orientation in which the local route of the blood vessel is seen to be the most widespread. Therefore, according to the present embodiment, the three-dimensional image V0 can be displayed so as to have an orientation in which the travel state of the blood vessel can be appropriately observed.

Further, in the present embodiment, in a case where the reference point is moved, the interpolation display planes interpolated between the display planes based on the reference points before and after the movement are displayed, and the three-dimensional image V0 is projected onto the interpolation display planes. Therefore, the orientation of the three-dimensional image V0 in a case where the reference point is moved can be smoothly changed.

In the above-described embodiment, the plane setting unit 24 sets the plane having the orientation in which the sum of the distances from the plurality of points set in the local route is minimized, as the display plane, but the present disclosure is not limited thereto. The plurality of points set in the local route may be projected, and in the projected plane, a plane having the orientation in which the variance of the projected points is maximized may be set as the display plane. In this case, the plane setting unit 24 defines a certain plane as an initial plane, and projects the plurality of points set in the local route onto the plane defined as the initial plane, to convert the points on the three-dimension into the points on the two-dimension. Then, in order to obtain the variance of the converted points on the two-dimension, the plane setting unit 24 optimizes the orientation of the plane so that the variance of the points on the two-dimension is maximized. The variance of the points on the two-dimension has, for example, a covariance value.

Further, in the above-described embodiment, in a case where the plane setting unit 24 projects the plurality of points included in the local route, the plane having the orientation in which the distribution of the projected points is maximized is set as the display plane, but the present disclosure is not limited thereto. In a case where there is a reference value based on the maximum value, a reference value based on a value smaller than the maximum value by about several %, for example, about 20% may be used.

In the above-described embodiment, the range centered on the reference point P0 set by the local-route extraction unit 23 may be changeable in response to the instruction through the input unit 15.

Further, in the above-described embodiment, the reference point is moved in response to the instruction through the input unit 15 by the operator, but the present disclosure is not limited thereto. The reference point may be automatically moved from the start point Ps to the target point Pe at a predetermined speed. In this case, the local-route extraction unit 23 extracts a new local route in response to the movement of the reference point, the plane setting unit 24 sets a new display plane, and the display control unit 25 projects the three-dimensional image V0 onto the new display plane and displays the ray-sum image on the display unit 14.

Further, in the above-described embodiment, the core-line extraction unit 22 extracts the core line of the blood vessel, but the designation of the position of the core line in the three-dimensional image V0 using the input unit 15 by the operator may be received and the core line in the designated position may be extracted. The designation of the core line may be performed, for example, through the display of the three-dimensional image V0 on the display unit 14 using a method such as volume rendering, and the reception of the instruction of the operator using the input unit 15 for the displayed three-dimensional image V0.

Further, in the above-described embodiment, the aorta and the artery branching from the aorta are set as the area to be diagnosed, but the present disclosure is not limited thereto. For example, the present embodiment can be applied to the case where another blood vessel, such as a coronary artery or a cerebral artery, is used as the area to be diagnosed.

Further, in the above-described embodiment, the CT image is used as the three-dimensional image V0, but the present disclosure is not limited thereto, and an MRI image, a PET image, or the like may be used.

Further, in the above-described embodiment, for example, as a hardware structure of a processing unit that executes various processing such as processing performed by the image acquisition unit 21, the core-line extraction unit 22, the local-route extraction unit 23, the plane setting unit 24, and the display control unit 25, the following various processors may be used. The various processors include, for example, a programmable logic device (PLD), such as a field programmable gate array (FPGA), which is a processor having a changeable circuit configuration after manufacture, and a dedicated electrical circuit, such as an application specific integrated circuit (ASIC), which is a processor having a dedicated circuit configuration designed to perform specific processing, in addition to the CPU which is a general-purpose processor that executes software (program) to function as various processing units as described above.

One processing unit may be constituted of one of the various processors or may be constituted of a combination of two or more processors of the same type or different types (for example, a combination of a plurality of FPGAs and a combination of a CPU and an FPGA). Further, the plurality of processing units may constitute one processor.

A first example of the configuration in which the plurality of processing units are formed by one processor is an aspect in which one or more CPUs and software are combined to form one processor and the processor functions as a plurality of processing units. A representative example of the aspect is a computer such as a client and server. A second example of the configuration is an aspect in which a processor that implements all of the functions of a system including the plurality of processing units with one integrated circuit (IC) chip is used. A representative example of the aspect is a system on chip (SoC). As such, as the hardware structure of various processing units, one or more of the various processors are used.

Further, as the hardware structure of the various processors, more specifically, an electrical circuit (circuitry) in which circuit elements such as semiconductor elements are combined may be used.

EXPLANATION OF REFERENCES

1: image orientation setting apparatus
2: three-dimensional image capturing apparatus
3: image storage server
4: angiography apparatus
5: network
11: CPU
12: memory
13: storage
14: display unit
15: input unit
21: image acquisition unit
22: core-line extraction unit
23: local-route extraction unit
24: plane setting unit
25: display control unit
30: contrast-enhanced blood vessel region
41: main body
42: C arm
43: attachment portion
44: radiation source
45: imaging unit
46: imaging table
47: display unit
A0: sphere
C0: core line
L0, Ls: local route
M1 to M3: plane
M11, M12: display plane
MH1 to MH3: interpolation display plane
Mb: reference display plane
O1 to O3: point on local route
P0: reference point
Ps: start point
Pe: target point
R0 to R3: ray-sum image
V0: three-dimensional image
V1: partial three-dimensional image

What is claimed is:

1. An image orientation setting apparatus comprising:
a processor that is configured to
extract a core line of a blood vessel from a three-dimensional image of a subject including the blood vessel,
extract a local route of the core line within a predetermined range based on a reference point on the core line, and
in a case where a plurality of points on the local route are projected, set a plane among a plurality of tentative planes having different orientations as a display plane of the three-dimensional image, wherein the plane set as the display plane has an orientation in which a sum of distances from each of the plurality of points to the plane is minimized.

2. The image orientation setting apparatus according to claim 1,
wherein the processor is configured to display a projected image in which the three-dimensional image is projected onto the display plane, on a display.

3. The image orientation setting apparatus according to claim 1,
wherein in a case where the reference point is moved, the processor is configured to
extract the local route within the predetermined range based on the moved reference point, and
set a second display plane on the basis of the local route extracted within the predetermined range based on the moved reference point.

4. The image orientation setting apparatus according to claim 3,
wherein the processor is configured to display a first projected image and a second projected image on a display, the first projected image is a projected image in which the three-dimensional image is projected onto a first display plane set on the basis of the local route extracted within the predetermined range based on the reference point before the movement, and the second projected image is a projected image in which the three-dimensional image is projected onto the second display plane set on the basis of the local route extracted within the predetermined range based on the reference point after the movement.

5. The image orientation setting apparatus according to claim 3,
wherein the processor is configured to generate at least one interpolation display plane that is interpolated between a first display plane and the second display plane, the first display plane set on the basis of the local route extracted within the predetermined range based on the reference point before the movement, and the second display plane set on the basis of the local route extracted within the predetermined range based on the reference point after the movement.

6. The image orientation setting apparatus according to claim 5,
wherein the processor is configured to display a first projected image, a second projected image and an interpolation projected image on a display, the first projected image is a projected image in which the three-dimensional image is projected onto the first display plane, the second projected image is a projected image in which the three-dimensional image is projected onto the second display plane, and the interpolation projected image is a projected image in which the three-dimensional image is projected onto the interpolation display plane.

7. The image orientation setting apparatus according to claim 1,
wherein the processor is configured to change a range of the local route in response to a change instruction of the predetermined range.

8. The image orientation setting apparatus according to claim 1,
wherein the reference point is located between a start point and a target point set on the core line,
wherein the start point is a branch position of an artery that the catheter first reaches, and
wherein the target point is a position in which the catheter reaches and an examination or a treatment is performed.

9. The image orientation setting apparatus according to claim 1,
wherein the processor is configured to emphasize the blood vessel of a projected image in which the three-dimensional image is projected onto the display plane, and display the projected image on a display.

10. The image orientation setting apparatus according to claim 9,
wherein the processor is configured to emphasize the blood vessel with the core line superimposed thereon, and display the projected image.

11. The image orientation setting apparatus according to claim 9,
wherein the processor is configured to emphasize the local route in the core line, and display the projected image.

12. The image orientation setting apparatus according to claim 1,
wherein the processor is configured to
set a tentative plane projecting a plurality of points on the local route,
calculate a sum of distances from the tentative plane to each of the plurality of points,
repeat to change an orientation of the tentative plane and to calculate a sum of distances from a tentative plane with the changed orientation to each of the plurality of points to obtain the plurality of calculated sums of distances respectively corresponding to the tentative planes with the changed orientations, and
set a tentative plane having an orientation in which the calculated sum of the distances is a minimum among all the calculated sum of distances as the display plane of the three-dimensional image.

13. An image orientation setting method comprising:
extracting a core line of a blood vessel from a three-dimensional image of a subject including the blood vessel;
extracting a local route of the core line within a predetermined range based on a reference point on the core line; and
in a case where a plurality of points on the local route are projected, setting a plane among a plurality of tentative planes having different orientations as a display plane of the three-dimensional image, wherein the plane set as a display plane has an orientation in which a sum of distances from each of the plurality of points to the plane is minimized.

14. A non-transitory computer readable recording medium storing an image orientation setting program causing a computer to execute a process comprising:
extracting a core line of a blood vessel from a three-dimensional image of a subject including the blood vessel;
extracting a local route of the core line within a predetermined range based on a reference point on the core line; and
in a case where a plurality of points on the local route are projected, setting a plane among a plurality of tentative planes having different orientations as a display plane of the three-dimensional image, wherein the plane set as a display plane has an orientation in which a sum of distances from each of the plurality of points to the plane is minimized.

15. An image orientation setting apparatus comprising:
a processor that is configured to
extract a core line of a blood vessel from a three-dimensional image of a subject including the blood vessel;
extract a local route of the core line within a predetermined range based on a reference point on the core line;
set a tentative plane projecting a plurality of points on the local route,
project the plurality of points onto the tentative plane,
calculate a variance of the plurality of projected points in the tentative plane,
repeat to change an orientation of the tentative plane and to calculate a variance of a plurality of projected points projected onto the tentative plane with the changed orientation to obtain the plurality of calculated variances respectively corresponding to the tentative planes with the changed orientations, and
set a tentative plane having an orientation in which the calculated variance is a maximum among all the calculated variances as the display plane of the three-dimensional image.

16. An image orientation setting method comprising:
extracting a core line of a blood vessel from a three-dimensional image of a subject including the blood vessel;
extracting a local route of the core line within a predetermined range based on a reference point on the core line;
setting a tentative plane projecting a plurality of points on the local route;
projecting the plurality of points onto the tentative plane;
calculating a variance of the plurality of projected points in the tentative plane;
repeating to change an orientation of the tentative plane and to calculate a variance of a plurality of projected points projected onto the tentative plane with the changed orientation to obtain the plurality of calculated variances respectively corresponding to the tentative planes with the changed orientations; and
setting a tentative plane having an orientation in which the calculated variance is a maximum among all the calculated variances as the display plane of the three-dimensional image.

17. A non-transitory computer readable recording medium storing an image orientation setting program causing a computer to execute a process comprising:
extracting a core line of a blood vessel from a three-dimensional image of a subject including the blood vessel;
extracting a local route of the core line within a predetermined range based on a reference point on the core line;
setting a tentative plane projecting a plurality of points on the local route;
projecting the plurality of points onto the tentative plane;
calculating a variance of the plurality of projected points in the tentative plane;
repeating to change an orientation of the tentative plane and to calculate a variance of a plurality of projected points projected onto the tentative plane with the changed orientation to obtain the plurality of calculated variances respectively corresponding to the tentative planes with the changed orientations; and
setting a tentative plane having an orientation in which the calculated variance is a maximum among all the calculated variances as the display plane of the three-dimensional image.

* * * * *